United States Patent [19]

Felix

[11] Patent Number: 4,716,764
[45] Date of Patent: Jan. 5, 1988

[54] METHOD AND DEVICE FOR DETERMINING THE CROSS-SECTION OF ELONGATED OBJECTS USING A SOUND FIELD

[75] Inventor: Ernst Felix, Uster, Switzerland

[73] Assignee: Zellweger Uster., Ltd., Switzerland

[21] Appl. No.: 776,880

[22] Filed: Sep. 17, 1985

[30] Foreign Application Priority Data

Oct. 26, 1984 [CH] Switzerland ............ 5160/84

[51] Int. Cl.⁴ ................................. G01N 29/00
[52] U.S. Cl. ............................. 73/571; 73/160; 73/579; 73/597
[58] Field of Search ............ 73/579, 599, 597, 584, 73/596, 160, 571

[56] References Cited

U.S. PATENT DOCUMENTS

| 2,538,444 | 1/1951 | De Mars | 73/599 |
| 3,750,461 | 8/1973 | Felix | 73/597 |
| 3,854,327 | 12/1974 | Felix | 73/584 |
| 4,581,935 | 4/1986 | Breazeale | 73/160 |

Primary Examiner—John Chapman
Attorney, Agent, or Firm—Antonelli, Terry & Wands

[57] ABSTRACT

For determining the cross-section of running yarns, rovings and slivers in the textile industry, or of cables and filaments a test object is passed through an enclosed sonic chamber in which standing waves of at least two frequencies are generated by sonic emitters and their state is sensed by sonic receivers. The cross-section of the test object is determined by changes caused by the test object to the standing wave with respect to amplitudes, phases and/or pulses compared with undisturbed wave propagation. The particular arrangement of sonic emitters and sonic receivers causes especially appropriate modes of standing waves to be generated which act with optimum influence on the test object. As the device is used directly on production machines, which experience unavoidable vibrations during operation, measures are provided for at least partial compensation of unwanted signals caused by vibrations in the sonic receivers by their appropriate location and reciprocal electrical connection.

1 Claim, 7 Drawing Figures

METHOD AND DEVICE FOR DETERMINING THE CROSS-SECTION OF ELONGATED OBJECTS USING A SOUND FIELD

BACKGROUND OF THE INVENTION

The present invention relates to measuring apparatus, and more particularly to a method and device for at least approximately determining the cross-section of elongated objects, especially yarns, rovings and slivers in the textile industry, and of cables or filaments.

A number of methods and devices are already known for determining the cross-section of elongated objects, such as yarns, rovings and silvers in the textile industry, and of cables or filaments. These known methods and devices are based on various physical principles. Those which have proved especially apt have been electro-optical and capacitive methods, and in recent times electro-acoustical methods, and these have resulted in a diversity of measuring systems.

The above-mentioned electro-acoustical methods have, however, not yet found widespread acceptance since the control of the sonic fields and evaluation of their variations resulting from the test object affecting their undisturbed propagation require extensive research into the most effective arraangement.

A first proposed solution for influencing an acoustic field by elongated objects consisting of fibers, especially yarns, rovings and slivers, and of cables or filaments, is to be found in my U.S. Pat. No. 3,750,461, issued on Aug. 7, 1973. There, the elongated object, hereinafter referred to as the test object, is passed through the zone of oscillation nodes or antinodes of a standing wave with the standing wave being propagated from resonance generators and aimed at the test object. The presence of the test object acts upon the standing wave in the sense of affecting the pulse timing or phase at the point of arrival of the test object, so that from the size of this change (by comparison with undisturbed propagation), it is possible to determine the cross-section of the test object.

A further development of this principle is disclosed in my U.S. Pat. No. 3,854,327, issued on Dec. 17, 1974. This describes a method in which the test object passes through a sonic field having two different frequencies, for example a basic frequency and double this basic frequency in superimposed sonic fields. In principle, one frequency would suffice, but it is advisable to use a second frequency in order to compensate for temperature effects and dirt deposits. In this regard, temperature changes and possible dirt deposits on the resonator walls affect the two frequencies relatively to approximately equal extents. The two frequencies may be emitted simultaneously at the sonic emitter or they may be emitted intermittently by means of commutation at the sonic emitter. In principle, measurement at one frequency alone may be adequate under most circumstances, for example. The second serves only to compensate interference sources which usually change slowly.

The electro-acoustic transducers acting as sonic emitters or sonic receivers are located on plane surfaces, the space between them being exposed or open to the atmosphere. The sound pressures existing in the standing wave then relate to the environmental atmospheric pressure.

Also this method and the corresponding apparatus are not free from limitations relating to their application. There are spinning techniques in which the test object (fibrous material) is carried by compressed air through a duct from one processing stage to the next and determination of the amount of fibrous material or of the cross-section is to be performed in this duct zone, as it is not possible to provide a measuring unit at any other place. However, the use of compressed air prohibits the passage of the test object through a test unit which is open at one or both sides.

Furthermore, measuring units operating on the principles explained above cannot be applied if they are mounted directly onto production machines. The measuring units tend to be undesirably shaken by the inevitable machine vibrations and there are no acoustic receivers which do not react unfavorably to such vibrations, especially as they must be built in the form of highly sensitive transducers.

Measuring units in accordance with the developments described as the state of the art can thus only be used with adequate precision in measuring apparatus set up at undisturbed locations (e.g. in laboratories) and provided for measuring test samples away from the production line. However, modern technologies demand constant monitoring directly during the production process in order to perform the necessary control and regulation of functions without delay on the basis of the test results.

SUMMARY OF THE INVENTION

It is an object of the present invention to provide a method and apparatus of the type described which avoids certain disadvantages of the prior art in an effective manner.

In accordance with the present invention, there is provided a method and an apparatus for at least approximately determining the cross-section of elongated objects, especially of yarns, rovings and slivers in the textile industry, and of cables of filaments by the use of sonic energy which is radiated by at least one sonic emitter and detected by at least one sonic receiver, with the test object being situated between the sonic emitter and the sonic receiver and thus influencing the propagation of the sound waves, a characteristic feature of which is that the sonic emitter and sonic receiver act on a sonic chamber enclosed laterally on all sides, through which the test object (1) passes.

In accordance with an advantageous feature of the invention, at least two sonic receivers are located and electrically connected in such a way that mechanical vibrations acting upon them are at least partially eliminated, but the sonic waves falling on them are added together. In one embodiment, a first sonic field produced between one sonic emitter and one sonic receiver in the longitudinal axis of the sonic chamber and a second sonic field between a further sonic emitter and a further sonic receiver produce standing waves in the longitudinal axis of the sonic chamber.

The sonic emitters act upon the sonic chamber in such a way and the frequencies adopted are such that in the sonic chamber oscillations are created with modes so that the elongated object passes through at least one node of a first mode and through at least one antinode of a second mode.

BRIEF DESCRIPTION OF THE DRAWINGS

Examples of various embodiments of the invention will be described in greater detail with reference to the accompanying drawings, in which.

DETAILED DESCRIPTION OF THE PREFERRED EMBODIMENTS

Figure 1:
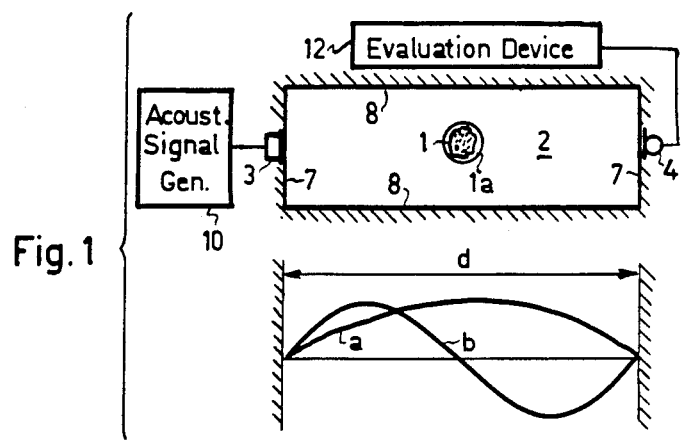
FIG. 1 is a diagram showing the basic arrangement for measurement of a strand of fibers in an enclosed acoustic resonator.

In FIG. 1, item 2 represents a sonic chamber enclosed laterally on all sides. Passing through the chamber 2 is the test object 1, which may take the form of a strand of fibers, a cable or a filament. As shown, the test object 1 is passed perpendicularly to the plane of the drawing. Of course, the front and rear walls of the sonic chamber which lie parallel to the plane od the drawing have appropriate apertures for the test object; however, this does not restrict the formation of standing waves in the sonic chamber.

On opposite facing walls 7 of the sonic chamber 2 there are built-in a sound source 3, for example a loudspeaker, and a sonic receiver 4, for example a microphone. If the sound source 3 is activated at an acoustic frequency by the acoustic signal source at a frequency or wave length λ (in air) which is in a certain ratio to the distance d between the walls, then standing waves are formed in the sonic chamber. If the wave length λ is twice the distance d, then at the wall surfaces there is an oscillation node and in the center (at λ/2) there is an oscillation antinode (curve a). If the frequency is doubled (i.e., the wave length λ halved) so that λ=d, then the standing wave of curve b functions with oscillation nodes at 0, d/λ and d, and with oscillation antinodes at ¼d and ¾d. The test object modifies the signal occurring at the receiver 4 in known fashion so that the size of the test object can be determined by the evaluation device from the change in the output signal of receiver 4 compared with that produced by an undisturbed standing wave pattern by evaluation of the amplitudes and/or phases and/or pulse differences.

Figure 3:
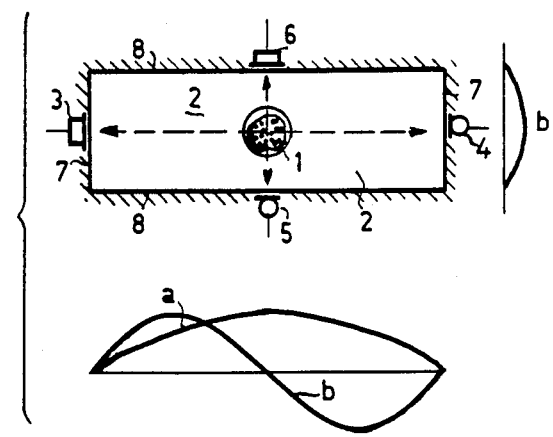
FIG. 3 is a diagram showing a strand of fibers in an acoustic resonator with sonic impulses in different axes.

As already disclosed in the aforementioned U.S. Pat. No. 3,854,327 at least two frequencies may be used for a comprehensive evaluation in order to be able to locate the test object 1 both in an oscillation antinode of the one frequency and in an oscillation node of the other frequency. It is thus advantageous to adopt frequencies in at least approximately whole-number ratios. FIG. 3 shows an example of this. The opposite-facing sonic emitter 3 and sonic receiver 4 or sonic emitter 6 and sonic receiver 5, respectively, cooperate. They are located on two opposing surfaces 7, 8 of the sonic chamber 2. Sonic emitter 3 generates a standing wave a and sonic emitter 6 generates a standing wave b orientated perpendicularly to the former. The test object which passes centrally through the chamber 2 is thus located at a pressure minimum (velocity maximum) of wave b and at a pressure maximum (velocity minimum) of wave a.

As mentioned above, operation at two frequencies is of advantage for compensating for interference, for example influences of temperature and deposits of dirt. If the temperature distribution int he sonic chamber is homogeneous, then it is possible to compensate for the influence of temperature when the oscillation directions at the two frequencies are different. The situation is otherwise, for example, with dirt deposits on the walls of the sonic chamber. These do not have an equal influence on the oscillations at the two frequencies. If the oscillations are in the same direction, then any dirt deposits that may be present on the walls tend to have an equal influence on the two frequencies.

Figure 4:
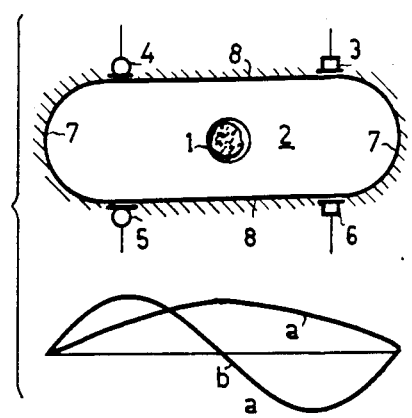
FIG. 4 is a diagram which shows another form of acoustic resonator.

The sonic chamber 2 need not necessarily be of rectangular cross-section. It may also be of a different cross-sectional form, as shown in FIG. 4. This can be advantageous, for example, for constructional reasons. FIG. 4 simultaneously shows also another configuration of emitters 3, 6 and receivers 4, 5. The lateral walls 7 are semi-circular in shape. Emitters 3, 6 can here be in parallel and activated in such a way to create a basic oscillation a. This basic oscillation can simultaneously be superimposed with a second frequency, thus creating a harmonic wave b. The receivers 4, 5 may be in parallel and receive both the pressure signal of the basic wave a in phase opposition (180°) to the emitter signal and also the first harmonic wave b in phase (i.e., at 2×180° phase shift).

Figure 2:
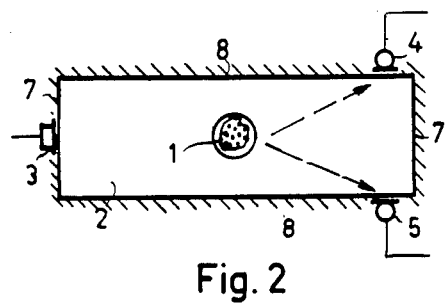
FIG. 2 is a diagram which shows the form of a resonator for compensating vibrations.

When such electro-acoustical measuring units are fitted on production machines, shaking is experienced through machine vibrations. There are practically no acoustic receivers which do not react to vibrations. Their susceptibility to vibrations is considerable, especially in a direction perpendicular to the transducer membrane. In the example of an embodiment in accordance with FIG. 2, two sonic receivers 4, 5 are located opposite each other. If these receivers are of equal polarity and in parallel, signals caused by mechanical vibrations are nullified, while the sound waves of the natural oscillations in the longitudinal direction coincide in mid-phase and are thus added together.

Figure 6:
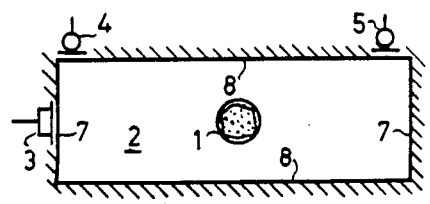

Interference can also be caused by noise outside the measuring unit. Compensation is alos possible here by appropriate arrangement of the microphones. FIG. 6 shows a corresponding example. The microphones 4, 5 are located practically at opposite sides of the resonator. When operting at the basic wave, the pressure maxima are in phase opposition tot he microphones 4,5. They can thus be also interconnected in phase opposition. External noise, however, tends to come in phase to the two microphones. However, as their polarity is in phase opposition, this interference noise is not received. The location adopted for the microphones is to meet the end-use so that interference vibrations or noise can be best compensated.

According to th arrangement explained in page 5 of Swiss Patent CH-PS No. 543.075 corresponding to U.S. Pat. No. 3,854,327 with sound panels facing each other, open above and below, it is only possible to produce standing waves if their half wavelength constitutes a whole-number ratio of the distance between the sound source and the sonic receiver. In the present method, with the sonic chamber enclosed laterally on all sides there are additional possibilities for generating specific oscillation conditions within the sonic chamber, called modes. The formation of such modes is well known and is published for example in Philip M. Morse and K. Uno Ingard, Theoretical Acoustics, pages 467-522 and 544-576 (McGraw Hill, 1968);

Bergmann-Schaefer, Lehrbuch der Experimentalphysik, Vol. 1, pages 492-504 (Walter de Gruyter & Co., 1974).

The objective is now to adopt sonic chamber dimensions and frequencies emitted by the sonic emitters 3, 6 for a mode to be generated which, with regard to the test object 1, produces the maximum influence on the signal received by the sonic receiver 4 or sonic receivers 4, 5.

Figure 5:
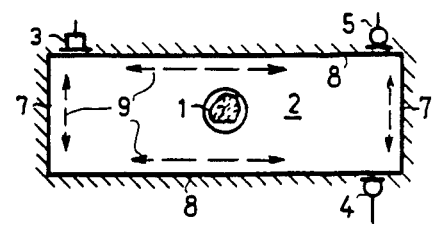
FIGS. 5 and 6 are diagrams showing different forms of a resonator for compensating vibrations.

A possible arrangement is shown in FIG. 5. The sonic emitter 3 produces a so-called mixed oscillation mode, the direction of oscillation of which is indicated by the arrow 9. At the sonic receiver 4 a signal is received in phase with the emitted signal. The test object then lies in a pressure minimum and thus has practically no influence on the natural frequency of the mode. A further sonic receiver 5 is also located in a pressure minimum and supplies practically no signal. The sonic emitter 3 can now only be operated in such a way that also the first upper wave occurs in the longer lateral direction. The test object then lies in the pressure maximum (or velocity minimum) of this wave. The sonic receiver 5 is only sensitive to the signal of this state of oscillation.

Figure 7:
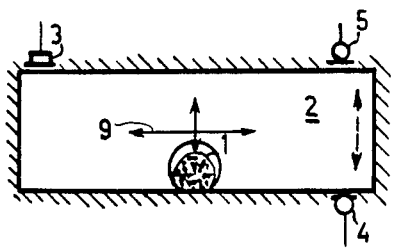
FIG. 7 is a diagram of a resonator analogous to that shown in FIG. 5 with the test object passed through off-center.

FIG. 7 shows a form of the resonator in accordance with FIG. 3 or FIG. 1, in which the test object 1 passes along one perimeter wall 8 of the sonic chamber 2, thus coming into contact with it. In practice this is the normal arrangement for the test object as it is difficult to pass the test object through in suspension without undue tension in the center of the sonic chamber. With regard to the influence on the sonic field, the same remarks apply as given above in the explanation of FIG. 5.

While we have shown and described several embodiments in accordance with the present invention, it is understood that the same is not limited thereto but is susceptible of numerous changes and modifications as known to one having ordinary skill in the art and we therefore to not wish to be limited to the details shown and described herein, but intend to cover all such modifications as are encompassed by the scope of the appended claims.

I claim:

1. A device for at least approximately determining the cross-section of elongated objects such as yarns, rovings and slivers in the textile industry, and cables or filaments comprising:

a sonic chamber enclosed laterally on all sides and having apertures in opposing walls to permit passage of an elongated test object through said chamber;

two sonic emitters positioned respectively on first and second walls of said chamber for radiating sonic energy from said first and second walls of said chamber into said chamber to create standing waves therein;

two sonic receivers positioned respectively on third and fourth walls of said chamber for detecting sonic energy within said chamber; and evaluation means connected to said sonic receivers for determining the cross-section of an elongated test object passing through said chamber on the basis of the influence of said test object on the standing waves within said chamber.

* * * * *